US00PP09170P

United States Patent [19]

Van de Meer

[11] Patent Number: Plant 9,170

[45] Date of Patent: Jun. 20, 1995

[54] HYBRID TEA ROSE PLANT NAMED 'TENNESEE'

[75] Inventor: Peter J. A. Van de Meer, Aalsmeer, Netherlands

[73] Assignee: Terra Nigra B.V., De Kwakel, Netherlands

[21] Appl. No.: 17,668

[22] Filed: Feb. 9, 1993

[51] Int. Cl.[6] ..... A01H 5/00

[52] U.S. Cl. ..... Plt./16

[58] Field of Search ..... Plt. 16

*Primary Examiner*—Howard J. Locker

[57] ABSTRACT

A new and distinct Hybrid Tea rose plant, particularly distinguished by its continuous production of medium-large, deep orange flowers borne singly on strong, upright stems on a sturdy bush of medium height having good quality foliage.

1 Drawing Sheet

1

The present invention relates to a new and distinctive variety of rose plant of the Hybrid Tea class, which was originated by my crossing "Eliora" as the seed parent with "Cocktail" as the pollen parent (U.S. Plant Pat. No. 1,821). "Eliora" has a yellow color, longer stems, higher production, and has only been for sale in the Netherlands. "Eliora" has not been patented in the U.S.A.. "Coctail", has a yellow color, a bigger flower, moderate fragrance, and has longer stems than "Tennessee". "Tennessee" was germinated in 1985, in De Kwakel, The Netherlands. The plant is the result of breeding efforts carried on by me since 1984 in a specific breeding area in a greenhouse in De Kwakel, The Netherlands. The new plant resulted from my breeding efforts to improve quality, production, and vase life (improvement in comparison with the existing commercial available varieties) and to find new colors. The plant has been asexually reproduced by cuttings and grafting. "Tennessee" has been in commerce in The Netherlands since 1988. "Tennessee" has been commercially introduced in the United States in September 1993. Of the many cultivars known to me, there is no cultivar sufficiently similiar to "Tennessee" so as to provide a meaningful basis for comparison. All characteristics or defining features of the plant are faithfully reproduced and transmitted from one generation to the next and appear to be firmly fixed without any instability. Among the novel characteristics possessed by the new variety which distinguish it from its parents and all other varieties of which I am aware are:

(1) medium-large distinct deep orange flowers (2) continuous production of flowers (whole year round)

(3) strong dark green upright flower stem (4) upright plant of medium height with good quality foliage The accompanying drawing shows typical specimens of the vegitative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in the color description herein refers to plate numbers in the aforementioned color chart, e.g. "28B" is plate "28B" of the Royal Horticultural Society Colour Chart.

2

FLOWER

Blooming habit: Continuous; normally borne singly, one per stem.

Bud:

(1) *Size.*—Medium. Diameter of 2 cm. Depth or length of 3 cm.

(2) *Form.*—Long, pointed, opens normal.

(3) *Sepals.*—When the sepals first divide, the color is green. Inside: Center 145B, edges 146D. Outside: 144B with red brownish spot 181B. Number of Sepals: 5. Shape of sepals: Pointed. No extensions above the bud. Striae: No. Calyx: Funnel shaped. The aspect is smooth.

Bloom:

(1) *Size.*—Medium—diameter of 9 and depth of 3 cm.

(2) *Form.*—First open: cup form. Mature: first the shape is flat, then opens totally.

(3) *Petalage.*—30–40 petals.

(4) *Average number of blooms per stem.*—In soil: 25; In Rockwool 30.

Petals:

(1) *Texture.*—Semi-leathery.

(2) *Appearance.*—Satiny.

(3) *Arrangement.*—Regularly arranged.

(4) *Shape.*—The petal-edges curled back at the left and right sides of the petal. As a result the tip of the petal is pointed.

(5) *Outer petal.*—Round shaped. Diameter of 4 cm. Base: 4 mm. Color: orange with yellow. Early: 28A-B with margins 33A and the point of attachment 13A-14A. Mature: 33B-31B with point of attachment 13A-14A. Reverse side: Margin: curled back. Center: smooth. Base: 4 mm. Color: soft orange with yellow base. Early: 28A with point of attachment 14A. Mature: 30C with point of attachment 13A.

(6) *Inner petal.*—Pear shaped. Diameter of 3 cm. Base: pointed, 2 mm. Color: orange with yellow. Early: 33A with point of attachment 13A. Mature: 28A with point of attachment 14B. Reverse side: Smooth. Base: 2 mm. Color: soft orange with yellow. Early: 28A with point of attachment 14A. Mature: 25A with point of attachment 14A.

(7) *Petaloids.*—1 or 2. Color: orange with yellow base (28A). Size: 2 cm.

(8) *Lastingness.*—On the plant: 14 days. Cut flower: 9 days.
(9) *Fragrance.*—Very weak.

REPRODUCTIVE ORGANS

A. Stamens:
(1) *Arrangement.*—In a circle around the pistils.
(2) *Number.*—Average 110–120.
(3) *Filaments.*—Length 6–8 mm. Color: yellow 17A.
(4) *Anthers.*—Size 1.5–2 mm. Color: Yellow 16C.
(5) *Pollen.*—Yellow 16C.

B. Pistils:
(1) *Number.*—35–40.
(2) *Styles.*—Length: 6–7 mm. Color: yellow 8C.
(3) *Stigma.*—Yellow 8C.
(4) *Ovaries.*—Round shaped.

C. Hips:
(1) *Color.*—Orange.
(2) *Shape.*—Round.
(3) *Fertility.*—The fruit is fertile. The seeds are retained within the hips. There are only a few on the top of the hips.

PLANT

A. Form: Upright and branched.
B. Growth: Fast, average height after 1 year is 70–80 cm.
C. Foliage:
(1) *Size.*—Average 14 cm (7-leaflet leaf).

(2) *Shape.*—Oval pointed.
(3) *Margin type.*—Serrated.
(4) *Texture.*—Smooth.
(5) *Color.*—Upper side: dark green 131A. Under side: soft green 191B.
(6) *Leaflets.*—Number of leaflets on the compound leaf: 3 or 5 or 7. Size: 5–7 cm.
(7) *Stipules.*—No stipules can be found.
(8) *Petioles.*—7 cm. Color: green 147D.
(9) *Petiolule.*—1–2 mm.
(10) *Ribs.*—Soft green/white 145D.
(11) *Disease resistance.*—Normal resistance against Californian thrips and Spider mites. More sensitive towards mildew.

D. Thorns: The plant has a few thorns and prickles at the petioles.
*Thorn coloration.*—Immature: Red. Mature: Red (same intensity as immature).

E. Stem:
(1) *Length basal stem.*—60–70 cm.
(2) *Color.*—Dark green 143A.
(3) *Quality.*—Strong and upright.

I claim:

1. A new and distinct variety of Hybrid Tea rose plant, substantially as herein shown and described, characterized by its continuous production of medium-large, deep orange flowers borne singly on strong, upright stems on a sturdy bush of medium height having good quality foliage.

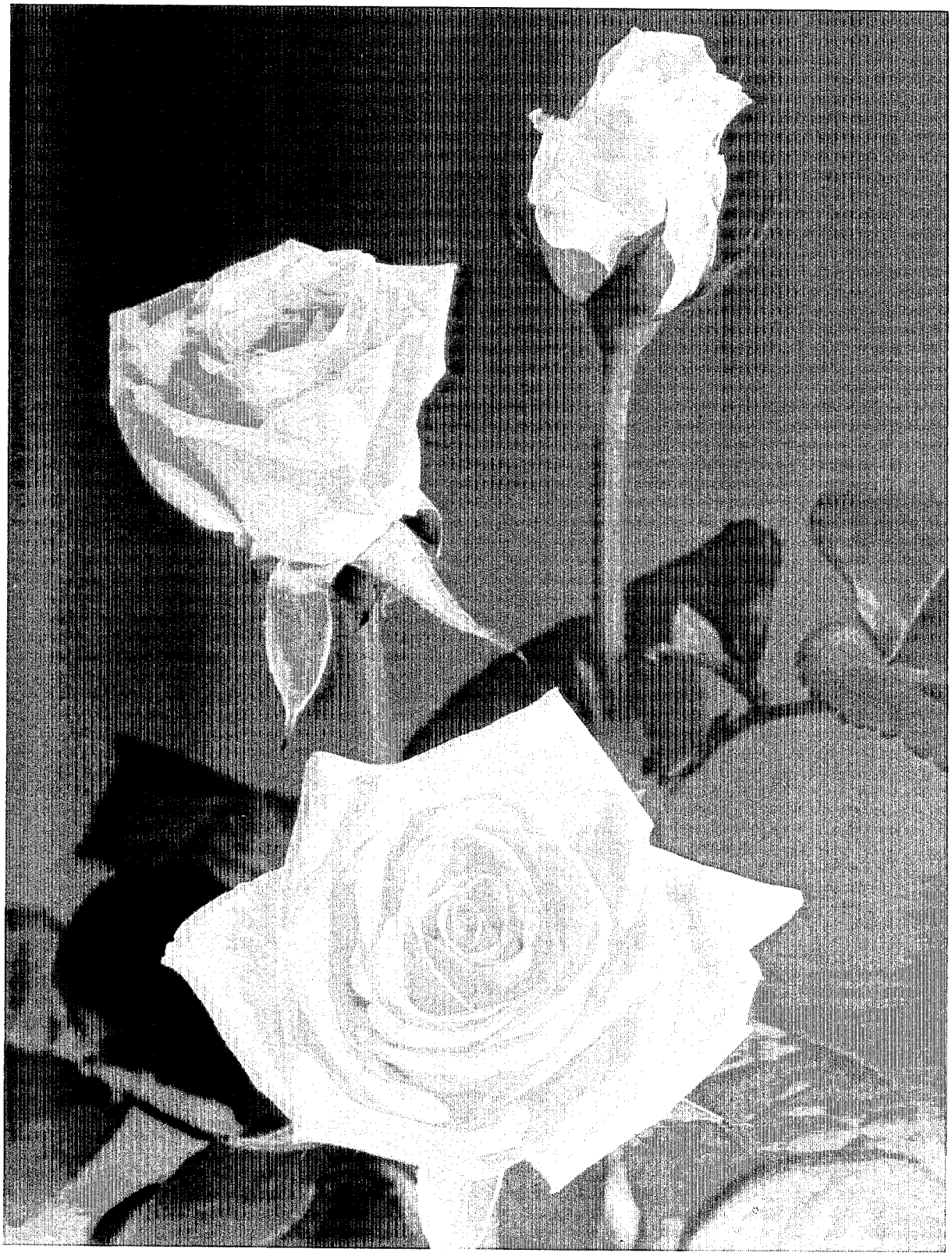

* * * * *